United States Patent
Abaev et al.

(10) Patent No.: US 6,581,443 B2
(45) Date of Patent: Jun. 24, 2003

(54) PROCESS FOR DETERMINING THE DISTILLATION CHARACTERISTICS OF LIQUID PETROLEUM PRODUCTS BY EXPRESS MINI-DISTILLATION AND APPARATUS PERMITTING IMPLEMENTATION OF THIS PROCESS

(75) Inventors: Guenrikh Abaev, Novopolotsk (BY); Raissa Andreeva, Novopolotsk (BY); Viachaslau Urvantsau, Novopolotsk (BY); Aliaksandr Spirydonau, Polotsk (BY); Victor Kalesnik, Polotsk (BY)

(73) Assignee: Instrumentation Scientifique de Laboratoire I.S.L. SA, Verson (FR)

( * ) Notice: Subject to any disclaimer, the term of this patent is extended or adjusted under 35 U.S.C. 154(b) by 0 days.

(21) Appl. No.: 09/981,314

(22) Filed: Oct. 17, 2001

(65) Prior Publication Data

US 2003/0037603 A1 Feb. 27, 2003

(30) Foreign Application Priority Data

Oct. 17, 2000 (FR) .............................................. 00 13270

(51) Int. Cl.$^7$ .............................................. G01N 25/02
(52) U.S. Cl. ........................ 73/61.77; 374/27; 700/270
(58) Field of Search .............................. 73/61.77, 61.76, 73/69.54; 374/27; 700/270

(56) References Cited

U.S. PATENT DOCUMENTS

| | | | | |
|---|---|---|---|---|
| 3,108,929 A | * | 10/1963 | Toliin et al. ................ | 73/61.76 |
| 3,794,566 A | * | 2/1974 | Raal ............................ | 374/27 |
| 4,250,739 A | | 2/1981 | Audeh | |
| 5,047,125 A | * | 9/1991 | Meier et al. ................ | 73/64.45 |
| 5,574,215 A | | 11/1996 | Bunger | |

FOREIGN PATENT DOCUMENTS

FR 2410818 *12/1977

OTHER PUBLICATIONS

Abaev et al. "Computer Complex for Modeling Fractional Distallation of Petroleum Products", Khimicheskoe I Neftyanoe Mashinostroenie, Apr. 1988, pp. 16–18.*

Dimuda et al. "Mathematical Model of Fractional Distillation of Petroleum Products and its Identification by Experimental Data", Inzynieria Chemiczna I Procesowa, 1996 No month, vol. 17, No. 4, pp. 635–644.*

Barrufet, M. A., "Evaluation of Standard PVT Properties from Equations of State", *Petroleum Engineer International, US*, Hart Publications; vol. 71, No. 5, mai 1998 (May 1998), pp. 49–50, 52–54, 56, XP000792941.

(List continued on next page.)

Primary Examiner—Hezron Williams
Assistant Examiner—Michael Cygan
(74) Attorney, Agent, or Firm—Kilpatrick Stockton LLP

(57) ABSTRACT

"Process for determining the distillation characteristics of liquid petroleum products by express mini-distillation and apparatus permitting implementation of this process"

Figure 1:
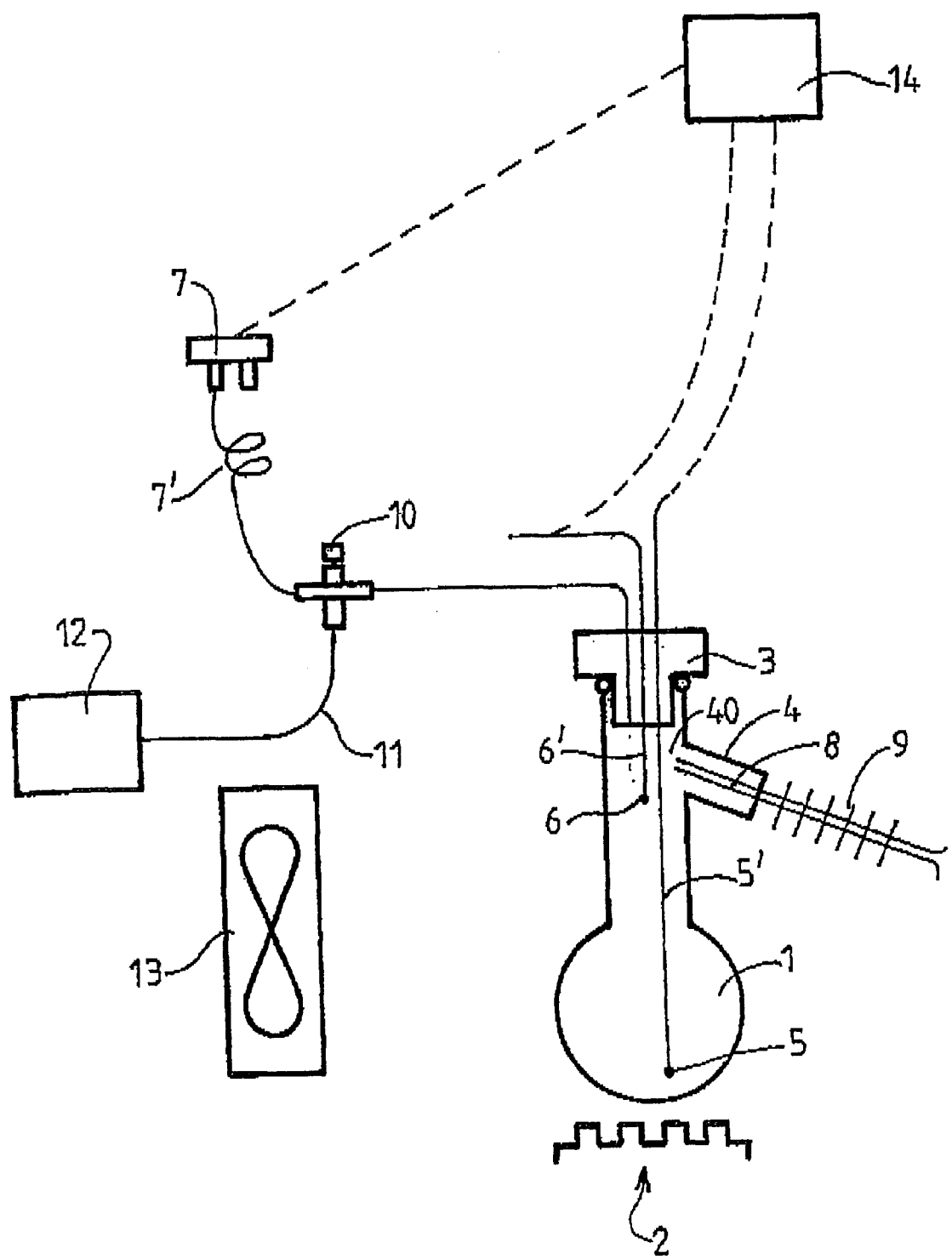

Apparatus characterized by the fact that it includes:
- a distillation flask dimensioned to receive 5 to 15 ml of a sample to be analysed,
- organs for heating the distillation flask, with an adjustable constant heating intensity,
- two inertialess temperature sensors permitting continuous measurement on the one hand of the true value of the temperature of a sample in the course of distillation in the liquid phase and the true value of the temperature of this sample in the vapor phase,
- a device for continuous measurement of the pressure in the vapor phase of a sample in the course of distillation which includes a pressure detector and a capillary tube, and
- organs for reception and exploitation of signals transmitted by the temperature sensors and the pressure detector.

10 Claims, 5 Drawing Sheets

OTHER PUBLICATIONS

W. Spieksma, "Prediction of ASTM Method D86 Distillation of Gasolines and Naphtas According to the Fugacity–Filmmodel from Gas Chromatographic Detailed Hydrocarbon Analysis"; *Journal of Chromatographic Science, US*; vol. 36, No. 9, Sep. 1, 1998, pp. 467–475, XP002100180.

Solimando, R., et al., "Etude D'Equations D'Etat En Vue De Representer Les Proprietes PVT ET Les Equilibres Liquide–Vapeur D'Hydrocarbures"; *Revue de L'Institut Francais Du Petrole, FR, Editions Technip*; vol. 50, No. 6, Nov. 1, 1995; pp. 791–05, XP000554827.

Abaev, G. N.; "Computer complex for Modeling Fractional Distillation of Petroleum Products"; Database accession No. EIX99464805338 XP002172449.

Zharkova, O.N.; "Additivity and Reciprocity of Fractional Distillation Parameters of Oil Products"; *Khim Tekhnol Topl Masel; Khimlya I Teknologiya Topliv I Masel*; May 1995, pp. 38–40; XP–002172450.

Spiridonov, A. V.; "Modeling of Oil Products Fraction Distillation, Taking into Account the Temperature Measurement Error"; *Khim Tekhnol Topl Masel: Khimiya I Tekhnologiya Topliv I Masel*; Jul.–Aug. 1998. pp. 41–43; XP002172451.

Spiridonov, A. V.; "True Boiling Point Curve Plotting Using Fractionation Data and Dynamic Errors of Temperature Measuring System"; *Khim Tekhnol Topl Masel; Khimiya I Tekhnologiya Topliv I Masel*; May–Jun. 1999; No. 3, mai 1999 (May 1999), pp. 37–39, XP002172452.

* cited by examiner

US 6,581,443 B2

PROCESS FOR DETERMINING THE DISTILLATION CHARACTERISTICS OF LIQUID PETROLEUM PRODUCTS BY EXPRESS MINI-DISTILLATION AND APPARATUS PERMITTING IMPLEMENTATION OF THIS PROCESS

The present invention relates to a process for determining the distillation characteristics of liquid petroleum products by express mini-distillation.

The volatility or more precisely the ranges of boiling temperatures of the different constitutive fractions of the petroleum products correspond to essential characteristic permitting characterisation of these products; these depend directly on the molecular weights of these fractions.

Currently the volatility of petroleum products is generally determined by physical tests under empirical conditions defined by standards, in particular the ASTM standards which are universally recognized by specialists.

By way of example, the standard ASTM D 86 permits determination of the volatility of light petroleum products having a boiling point lower than 400° C., while the standards ASTM D 1160 and ASTM D 2892 also permit determination of the volatility of heavy petroleum products having a higher boiling point. In this last case, it is sometimes necessary to have recourse to distillation under vacuum to lower the boiling temperatures of the products analysed and thus avoid their decomposition.

Analysis apparatus suitable for these standards have been known for many years. These function schematically in accordance with the following principle:

The sample to be analysed is introduced into a distillation flask provided with an outlet tube and this flask is closed by a bung provided with a thermometer.

This outlet tube is connected to a condenser tube co-operating with a cooling system and the outlet orifice of which is situated over a graduated reception test-tube. The flask is heated under predetermined conditions in order to bring the sample to boiling and the vapours formed are collected in the reception test-tube after condensation.

The temperature of the vapours present in the distillation flask is noted for predetermined volumes of condensate collected in the reception test-tube.

The curve is plotted giving the percentage of the volume of sample collected as a function of temperature and from this curve, which characterises the sample, it is verified whether this is in accordance with the required specifications.

It is to be noted that the temperature indicated by apparatus functioning in accordance with these standards do not always correspond to the true boiling temperatures but may correspond to empirical temperatures, taking into account the test conditions, in particular the thermometers used.

These apparatus which are currently used by all specialists to characterise liquid petroleum products allow reliable results with good reproducibility to be obtained, which are therefore representative of the sample analysed, but they do however have many disadvantages: they are in fact particularly heavy and bulky; moreover, the volume of sample required to perform a volatility test is relatively large (of the order of 100 ml) and the duration of each test is not less than 45 minutes.

To correct these disadvantages, in accordance with Byelorussian publication 198 0 801, researchers at the State University of Polotsk have already proposed a process and an apparatus permitting determination of the distillation characteristics of liquid petroleum products by physical tests each only lasting approximately 10 mn and each only requiring a much reduced volume of sample (of the order of 5 to 15 ml).

Another advantage of this process and this apparatus is linked to the fact that the characteristics of the product analysed are determined directly from temperature and pressure measurements and therefore they require no measurement of the volume of condensate collected in a reception test-tube.

The apparatus in accordance with this prior publication includes schematically a distillation flask co-operating with heating organs and which is provided with a capillary tube at the level of its outlet tube and is closed by a bung provided with a temperature sensor which is immersed in the boiling liquid and a differential sensor allowing measurement of the pressure in the vicinity of the capillary tube inlet.

The process employed upon use of this apparatus is based on a particular algorithm which permits calculation of the temperature of the vapour of the sample from its temperature of the vapour of the sample from its temperature in the liquid state in the distillation flask and from the rise in pressure within the latter consequent upon the presence of the capillary tube.

This method of determination of the distillation characteristics of the petroleum products has certain advantages.

However, the curves thus obtained have insufficient reliability taking into account the fact that the barometric pressure variations together with the residues in the distillation flask and the losses of sample in the vapour phase are not taken into consideration.

Moreover, the heating organs interfere with the measurement values of the temperature of the sample in the liquid phase.

Moreover, this method is only suited to the determination of the distillation characteristics of light liquid petroleum products having boiling temperatures lower than 400° C., and cannot be used for the determination of the distillation characteristics of heavy liquid petroleum products, since, operating at atmospheric pressure, they would cause thermal decomposition of these products.

The essential disadvantage of this method is however linked to the fact that the tests performed by it are not in correlation with the standards and in particular with the ASTM standards, which constitutes a major fault as these standards are currently universally recognised by specialists in the field of analysis of petroleum products.

The present invention has the object of correcting these disadvantages by proposing a process permitting determination of the distillation characteristics both of light liquid petroleum products and of heavy liquid petroleum products and their mixtures by express mini distillation so as to provide reliable and reproducible results in correlation with those from tests in accordance with the standards and in particular with the ASTM standards universally recognised by specialists.

In accordance with the invention, it has been possible to attain this end by means of a process including the following steps:

1. a volume of the order of 5 to 15 ml of the sample to be analysed is introduced into a distillation flask co-operating with a heavy element at its lower part and provided with a pressure detector and two inertialess temperature sensors permitting measurement on the one hand of the true value of the temperature of the sample in the liquid phase and on the other the true value of the temperature of the sample in the vapour phase at a level situated a little below the inlet of the outlet tube with which the distillation flask is equipped, 2. the distillation flask is heated with a constant heating intensity depending on the nature of the sample to be analysed so as to progressively boil it, 3. the vapour pressure in the distillation flask is constantly measured at the level of the inlet of the outlet tube, as are the true values of the temperatures of the sample in the liquid phase $T^L$ and the vapour phase $T^S$ and the curves are plotted representing the variations in the pressure and these temperatures as a function of time $\tau_1$, 4. the primary and secondary derivatives are established of the curve representing the variations of the temperature of the sample in the liquid phase and in the vapour phase:

$$\frac{dT^S}{d\tau_1}; \quad \frac{dT^L}{d\tau_1}; \quad \frac{d^2T^S}{d\tau_1^2}; \quad \frac{d^2T^S}{d\tau_1^2}$$

and the temperature is deduced of initial boiling in the liquid phase $T^L_{IBP}$ which corresponds to the point for which $$\frac{d^2T^L}{d\tau_1^2} = 0,$$

5. the temperature of initial boiling in the vapour phase $T^S_{IBP}$ is determined which corresponds to the time for which a commencement of increase of pressure is observed, 6. the temperature $T^L_{END}$ is determined for which the value indicated by the temperature sensor which measures the true value of the temperature of the sample in the liquid phase corresponds to the value indicated by the sensor which measures the temperature of the sample in the vapour phase and by convention this temperature $T^L_{END}$ is considered to be equal to the final boiling temperature in the vapour phase $T^S_{FBP}$, 7. the volumetric percentage of sample distilled $v_v$ is determined from curves representing the variations as a function of $\tau_1$ in the pressure of vapour P in the distillation flask and in the true value of the temperature of the sample in the vapour phase $T^S$ by the function:

$$v_{Vi} = \left[\frac{Sf(Ti^S, Pi)}{Sf(T^S, P)}, V_i^{res}\right]$$

in which $Sf(T^S, P)$ depends on the area situated below the pressure curve in the distillation process while $Sf(Ti^S, Pi)$ depends on the fraction of this area at the time $\tau_{li}$, and $V_i^{res}$ represents the volume of liquid in the distillation flask at the time $\tau_{li}$, 8. the molar percentage of sample distilled $V_M$ as a function of the true value of the temperature of this sample in the vapour phase $T^S$ is determined by the function $V_{ml}=f(v_{v1}, \rho_i, T^Si)$ in which $\rho_i$ represents the molar density at the time $\tau_{li}$, 9. the final boiling temperature in the liquid phase $T^L_{FBP}$ is determined by iteration in accordance with the formula:

$$T^L_{FBP} = T^L_{END} + \frac{(T^L_{END} - T^L_{FBP})}{\left[\frac{v_{END}}{(1-v_{END})}/a\right]} 1/k$$

in which $v_{END}$ represents the molar percentage of sample distilled at the temperature $T^L_{END}$ and a and k are coefficients in the mathematical model of distillation corresponding to the empirical formula:

$$v_M = \frac{a\tau^k}{(1+a\tau^k)}$$

calculated by iteration from the equation:

$$\ln\left(\frac{v_{Mi}}{1-v_{Mi}}\right) = \ln a + k \ln \tau_i$$

in which:

$$\tau_i = \frac{T^L_i - T^L_{IBP}}{T^L_{FBP} - T^L_i}$$

calculating at each step a new value of $T_{FBP}^L$ up to the moment when:

$$T_{FBP}^{L(n)} - T_{FBP}^{L(n-1)} \leq 1° \text{ C.}$$

10. the molar percentage of sample distilled as a function of the true value of the temperature of this sample in the vapour phase is recalculated so as to take account of the residues and losses of sample in the vapour phase by the formula:

$$v_{mi} = v'_{Mi} + \Delta Li + \Delta Si$$

in which $\Delta Si$ represents the percentage of vapour phase in the course of distillation, $\Delta Li$ the percentage of liquid phase at the moment of its formation by condensation and $v_{Mi}$ the molar percentage of sample distilled taking the residues into consideration, 11. the volumetric percentage of sample distilled $v_{Vi}$ as a function of the true value of the temperature of this sample in the liquid phase is determined by the formula:

$$v_{Vi} = F(v_{Mi}, \rho_i, T_i^L)$$

12. and the corresponding curve is plotted.

It is to be noted that the mathematical model of distillation corresponding to the empirical formula:

$$v_M = \frac{a\tau^k}{(1+a\tau^k)}$$

is detailed in the publication Dimudu T. A., Jarkova O. N. and Abaev G. N. Mathematical model of fractional distillation of petroleum products and its identification by experimental data // Inzynieria Chemiczna i Procesowa, 1996, V.17, N 4.

It is moreover to be noted that the experimental data obtained by the above-mentioned process correspond to a standard distillation technique in a column with one single plate called LBD distillation (Laboratory Batch Distillation) or FD distillation (Fractional Distillation).

In accordance with another characteristic of the invention, the heating intensity of the heating element is adjusted depending on the nature of the sample to be analysed so that the time necessary for distillation of it is of the order of from 5 to 15 minutes.

In the case of a sample having totally unknown characteristics, this power can where necessary be determined in a preliminary distillation step.

In accordance with another characteristic of the invention, the empirical value $T_{stand}$ of the temperature of the sample in the vapour phase corresponding to a standard is determined from the value $T^L$ of the temperature of the sample in the liquid phase calculated at steps 1 to 12 by the formula:

$$T_{iSTAND} = T_i^L - \theta_i$$

in which θ is a function which represents the difference between these temperatures.

The process in accordance with the invention is particularly well suited to determining the distillation characteristics of light liquid petroleum products in correlation with the standard ASTM D 86.

In this case, and in accordance with another characteristic of the invention:

$T_{STAND}^{D\,86}$ is the empirical temperature corresponding to the standard ASTM D 86 and $\theta_i^{D86}$ is calculated from the function:

$$\theta_i^{D86} = f\left(\frac{dT_i^L}{dv_{Vi}}, T_i^L, v_{vi}\right)$$

and is determined either graphically, or from values of the parameters (a, k, $T_{IBP}^L$, $T_{FBP}^L$), calculated in steps 1 to 12.

The process in accordance with the invention can also be adapted to determining the distillation characteristics of heavy liquid petroleum distillation products having boiling temperatures higher than 400° C., at atmospheric pressure, without reaching temperatures for which there would be a risk of coming up against thermal decomposition of the analysed product.

To this end, and in accordance with another characteristic of the invention:

- a light vehicle liquid petroleum product is selected having a boiling temperature below 300° C. compatible with the sample to be analysed,
- this vehicle liquid is subjected to steps 1 to 12 so as to obtain the curve representing the molar percentage $V_M$ of vehicle liquid distilled as a function of the true temperature of this liquid in the liquid phase $T^L$ $v_{Mi\,(vehicle)} = f(T_i^L)$,
- a mixture is prepared containing approximately 85 to 95% of vehicle liquid and 5 to 15% sample to be analysed so that at least 90% of this mixture has a boiling temperature lower than 360° C.,
- this mixture is subjected to steps 1 to 12 so as to plot the curve representing the molar percentage $V_M$ of this mixture distilled as a function of the temperature $T^L$ of the mixture in the liquid phase $v_{Mi(mix)} = f(T_i^L)$ in the same system of co-ordinates as the curve $v_{Mi(vehicle)} = f(T_i^L)$,
- it is considered by convention that the final boiling temperature $T_{FBP}^{HP}$ of the sample to be analysed is equal to the final boiling temperature of the mixture in the liquid phase, $$T_{FBP}^{HP} = T_{FBP}^L \text{ (mix)}$$

$T_{FBP}^L$ (mix is determined by iteration in accordance with steps 1 to 9, the initial boiling temperature in the liquid phase $T_{IBP}^{HP}$ of the sample to be analysed is calculated by the formula:

$$T_{IBP}^{HP} = T_1 - \Delta T_1 \left[\frac{v_{M1}}{a^{HP}(1-v_{M1})}\right]^{1/k^{HP}}$$

in which $T_1$ represent the temperature of intersection of the curves $v_{Mi(vehicle)} = f(T_i^L)$ and $v_{Mi(mix)} = f(T_1^L)$, $v_{M1}$ the molar percentage of sample which corresponds to this temperature $T_1$ et $\Delta T_1 = T_{FBP}^{HP} - T_1$ $a^{HP}$ and $k^{HP}$ are determined using the system of additive equations:

$$\Sigma\, v_{Mi} Si\, (T^L, a_i, k_i) = S^{mix}\,(T^L, a^{mix}, k^{mix}) \text{ and}$$

$$\Sigma\, v_{Mi} Si\, (\tau) = S^{mix}\,(\tau)$$

in which Si(T) and Si (τ) are function of the respective areas situated below the distillation curves in the systems of co-ordinates $v_M$, T and $v_M$, τ and Σ is a function of the specific gravity of the vehicle product in the mixture, and the curves $v_M^{HP} = f(T)$ are plotted from the formula:

$$v_M^{HP} = \frac{a^{HP} \tau^{k^{HP}}}{(1 + a^{HP} \cdot \tau^{k^{HP}})}.$$

For the sake of simplification, a well known product such as kerosene and/or a liquid petroleum product having a boiling point lower than 300° C. is generally used a vehicle.

In addition to the normal LBP or FD distillation techniques, the specialists in the field of analysis of petroleum products sometimes have recourse to distillation techniques corresponding to columns with a plurality of theoretical plates, generally at least fifteen theoretical plates called TBP (True Boiling Point) true distillations, which are also defined by universally recognised standards.

Now, the present invention also permits plotting of the curves of the TBP true boiling points of a sample, in particular in order to know its composition.

To this end, and in accordance with another characteristic of the invention:

- from LBP standard distillation curves $v_M = f(T)$ corresponding to a column with a single plate, the curves of the TBP true boiling points are plotted corresponding to a technique with a column with at least 15 theoretical plates, considering by convention that the temperatures $T_{END}^L$ (LBP) and $T_{END}^L$ are equal, that in the system of co-ordinates $v_M$, T the surfaces situated below the LBP standard distillation curves are equal to the areas situated below the curves of the TBP true boiling points and that $T_{IBP}(TBP) = f(S_{LBP})$, $f(S_{LBP})$ depending on the area situated below the LBP standard distillation curve in the system of co-ordinates $v_M$, T.

The invention also relates to an apparatus permitting implementation of the above-mentioned process.

In accordance with the invention, this apparatus is characterised by the fact that it includes

- a distillation flask dimensioned to receive from 5 to 15 ml of a sample to be analysed and provided at its upper part with a bung and a lateral outlet tube co-operating with a condenser,
- organs for heating the distillation flask, at its lower part, with an adjustable constant heating intensity, two inertialess temperature sensors introduced into the distillation flask through tubes passing through the bung so as to permit continuous measurement, on the one hand of the true value of the temperature of a sample in the course of distillation in the liquid phase and on the other the true value of the temperature of this sample in the vapour phase at a level situated a little below the inlet of the outlet tube, a device for continuous measurement of the pressure in the vapour phase of a sample in the course of distillation which includes a pressure detector connected to the internal part of the distillation flask by a pipe passing through the bung and a capillary tube introduced into the internal part of the outlet tube at the level of the inlet of this tube, and organs for reception and exploitation of signals transmitted by the temperature sensors and the pressure detector.

Taking these characteristics into account, to perform a test the user introduces 5 to 15 ml of sample to be analysed into the distillation flask, for example by means of a syringe, and the recloses this before selecting a heating intensity.

The organs for reception and exploitation then automatically switch the circuits associated with the temperature and pressure differential sensors and the heating and distillation of the sample commence.

During distillation, the different sensors continuously transmit to the organs for reception and exploitation signals which enable them to automatically create the distillation curves and display these curves on a screen and print them, this in a time less than fifteen minutes.

Depending on the field of the user for whom it is intended, the distillation flask, without thereby departing from the scope of the invention, may be either a permanent flask made in particular of glass or stainless steel, or a disposable flask, in which case the capillary tube is formed by a fixed element preferably made of stainless steel.

In accordance with another characteristic of the invention, the apparatus forms a portable, one-piece assembly.

This is a particularly advantageous characteristic as it allows an apparatus to be obtained of much reduced weight and volume able to very rapidly perform tests on petroleum products on any site, in particular in theatres of operation in the military field.

The characteristics of the process and the apparatus which form the object of the invention will be described in more detail with reference to the attached FIG. 1, which is a diagrammatic view showing an example of configuration of this apparatus.

As shown in FIG. 1, this includes a distillation flask 1 of spherical form provided with a lateral outlet tube 4 which is dimensioned to receive 5 to 15 ml of a sample to be analyzed.

This flask 1 is heated at its lower part with an adjustable constant heating intensity by a heating resistance 2 and is hermetically closed at its upper part by a removable bung 3 through which the sample to be analysed can be introduced, in particular by means of syringe.

Two inertialess temperature sensors 5, 6 are introduced into the distillation flask 1 through pies 5', 6' passing through the bung 3.

The first temperature sensor 5 is immersed in the liquid to be analysed to allow continuous measurement of the true value of the temperature of this sample, in the course of distillation in the liquid phase.

The second distillation sensor 6, for its part, is mounted at the upper part of the distillation flask 1, at a level situated a little below the inlet 40 of the outlet tube 4, so as to allow continuous measurement of the true value of the temperature of the sample in the course of distillation in the vapour phase.

The apparatus also includes a device for continuous measurement of the pressure in the upper part of the distillation flask 1.

As shown in FIG. 1, this device essentially consists of a pressure differential sensor 7 which is connected to the internal part of the distillation flask 1 by a flexible pipe 7', also passing through the bung 3.

The differential pressure sensor 7 co-operates with a metal capillary tube 8 introduced into the internal part of the outlet tube 4 of the distillation flask 1, so that the vapours of sample in the course of distillation escape to the outside through this capillary tube 8.

This is mounted so as to open into the distillation flask 1 at the level of the inlet 40 of the outlet tube 4 and is connected at its opposite end to an air condenser 9 permitting condensation of the vapours escaping from the distillation flask 1 to transfer them into a recovery element which is not shown.

The configuration of the outlet tube 4 of the distillation flask 1, of the capillary tube 8 and of the condenser 9 are so selected that the condenser which is screwed in during assembly of the apparatus compresses the capillary tube and creates the seal at the level of the exit of the vapours from the distillation flask 1.

Moreover, the pipe 7' for connection of the pressure differential sensor 7 and the internal part of the distillation flask 1 is provided with a T joint 10 including a flow limiter which is not shown at its internal part; to this joint 10 is connected an auxiliary pipe 11 connected to a microcompressor 12 so as to blow a small flow of air into the pipe 7', allowing prevention of the signals emitted by the pressure differential sensor 7 from being falsified by the introduction of condensate into the pipe 7'.

A fan 13 allows cooling of the distillation flask 1 after each test.

As shown diagrammatically in broken lines in FIG. 1, the signals emitted by the differential pressure sensor 7 and by the first and second temperature sensors 5 and 6 are transmitted to organs for reception and exploitation 14 of these signals which print and display the distillation curves on a screen in response.

The reliability of the process and the apparatus in accordance with the invention have been verified by tests the results of which are collated below.

EXAMPLE 1

Determination of the Standard LED Distillation Characteristics of a Hexane-Isooctane Decane Mixture A - By the process in accordance with the invention A mixture was analysed having the following volumetric composition:

hexane 40% isooctane 55% decane 5%

10 ml of this mixture were introduced into the distillation flask of an apparatus in accordance with the invention. This flask was placed in the apparatus and provided with a capillary tube and an air condenser.

Then the distillation programme was started and the temperatures of the sample in the liquid phase $T^L$ and in the vapour phase $T^S$, together with the pressure P in the internal part of the flask, measured constantly.

The organs for reception and exploitation allowed continuous checking of the distillation programme and calculation of the LED standard distillation characteristics of the mixture in accordance with the process in accordance with the invention.

The results obtained are collated in table 1 below and shown in the attached FIG. 2.

| $v_v$ | IBP | 0.05 | 0.1 | 0.2 | 0.3 | 0.4 | 0.5 | 0.6 | 0.7 | 0.8 | 0.9 | 0.95 | FBP |
|---|---|---|---|---|---|---|---|---|---|---|---|---|---|
| $T^S$ | 78.5 | 79.2 | 80.4 | 81.3 | 83.4 | 85.5 | 87.9 | 90.6 | 94 | 99.5 | 111.5 | 155.2 | 173.6 |
| $T^L$ | 81.7 | 82.5 | 83.4 | 83.8 | 86 | 88.5 | 91.5 | 95 | 100.1 | 107.2 | 130.8 | 174.4 | 175.6 |
| $T^{stand}$ | 75 | 78.3 | 79 | 80.4 | 81.7 | 83.4 | 85.3 | 88.1 | 91.6 | 96.6 | 105.2 | 128.7 | 168.7 |

Figure 2:
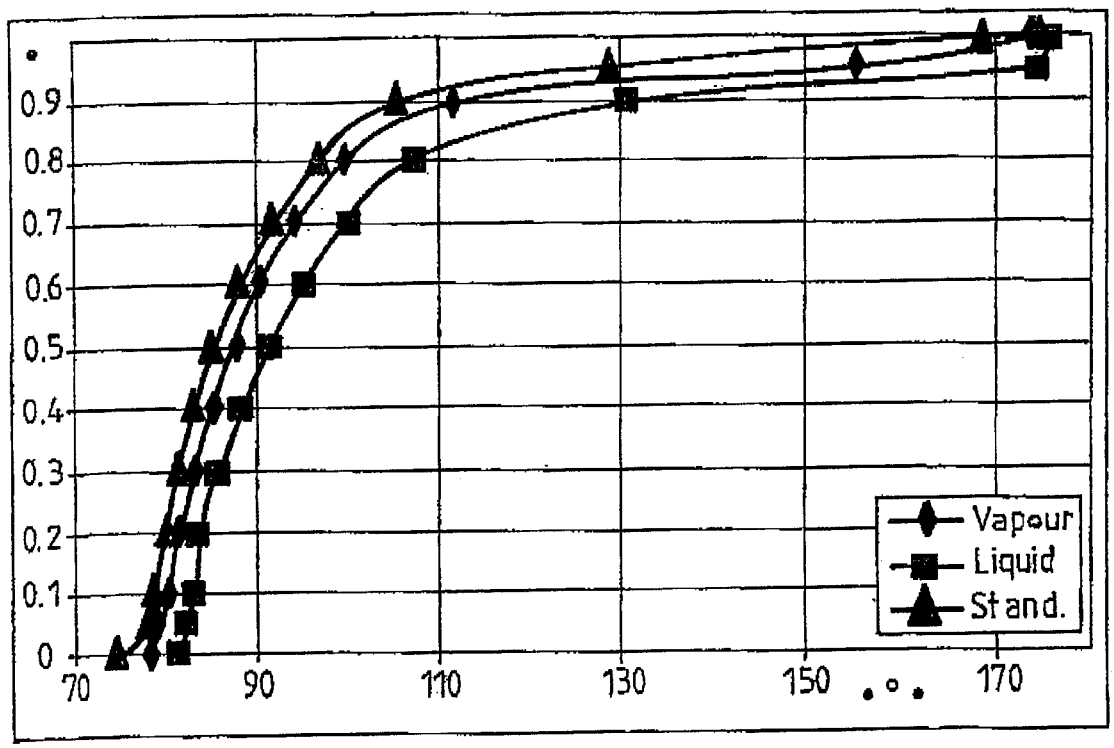

In table 1 and FIG. 2, the values $T^{stand}$ correspond to the temperature values recalculated as a function of standard ASTM D 86.

At the end of distillation, the heating organs were automatically switched off and the fan started in order to cool the distillation flask.

This test allowed a temperature $T_{FBP}$ of 173.6° C. to be obtained for the mixture, which is close the boiling temperature of pure decane, and a value $T_{IBP}^S$ of 78.5° C. and a value $T_{IBP}^L$ of 81.7° C.

At the end of distillation, the distillation flask was removed from the apparatus and a new sample to be analysed prepared.

B - By the process in accordance with the prior art corresponding to Byelorussian publication 198 0 801

The distillation of the same mixture as in test A was performed in a similar manner with the single exception that only the temperature $T^L$ of the mixture in the liquid phase was measured.

In accordance with this process, the volumetric percentages of sample distilled $v_V$ as a function of time $\tau 1$ were calculated using the following formula:

$$v_v = 0.92 \cdot \frac{\int_{T_{IBP}}^{T} (PT^S)^n d\tau_1}{\int_{T_{IBP}}^{T_{FBP}} (PT^S)^n d\tau_1} + 0.0005 \cdot (T_{IBP} - 20)$$

Then the temperature $T^{stand}$ was calculated from the temperature $T^L$ by the formula $T^{stand}=T^L-A$ in which A $$A = A_0 + A_1 \frac{ak}{T_{CP}} + A_2 v + A_3 \frac{ak}{T_{CP}} v + A_4 \left(\frac{ak}{T_{CP}}\right)^2 + A_5 v^2 + A_6 \left(\frac{ak}{T_{CP}}\right)^2 v^2$$

$A_1$, $A_2$, $A_3$, $A_4$, $A_5$ and $A_5$ being calculation coefficients while $T_{CP}$, represent the average boiling temperature.

The final boiling temperature $T_{FBP}$ was defined by the method of least squares in accordance with the equation:

$$\ln\left(\frac{v_M}{(1-v_M)}\right) = \ln a + k \cdot \ln \tau$$

and it was considered that the temperature $T_{FBP}$ corresponded to the temperature for which the minimum dispersion or maximum (coefficient of correlation) was observed.

The results obtained in accordance with this test are collated in table 2 below:

| $v_v$ | IBP | 0.05 | 0.1 | 0.2 | 0.3 | 0.4 | 0.5 | 0.6 | 0.7 | 0.8 | 0.9 | 0.95 | FBP |
|---|---|---|---|---|---|---|---|---|---|---|---|---|---|
| $T^L$ | 83.6 | 83.4 | 85.7 | 86.8 | 88 | 90.3 | 94.9 | 102 | 107.2 | 112.2 | 144.7 | 175.8 | 180.6 |
| $T^{stand}$ | 77.1 | 78.3 | 78.8 | 79.5 | 80.7 | 82.8 | 87.7 | 86.3 | 92.4 | 98.4 | 109.2 | 125.3 | 172.6 |

The temperature $T_{FBP}$ determined in accordance with this test differs from the final boiling temperature of pure decane by 6.5° C.

EXAMPLE 2

Determination of the LED Standard Distillation Characteristics of a Diesel Fuel

The same tests as in example 1 were carried out on a sample consisting of a diesel fuel using A the process in accordance with the invention and B the above-mentioned process in accordance with the prior art The results obtained in accordance with the tests performed in accordance with the invention are collated in table 3 below:

| $v_v$ | IBP | 0.05 | 0.1 | 0.2 | 0.3 | 0.4 | 0.5 | 0.6 | 0.7 | 0.8 | 0.9 | 0.95 | FBP |
|---|---|---|---|---|---|---|---|---|---|---|---|---|---|
| $T^S$ | 217.8 | 239.7 | 254.8 | 270.6 | 290.6 | 307.1 | 322.5 | 334.9 | 347.2 | 362.0 | 380.5 | 389.0 | 397.9 |
| $T^L$ | 226.6 | 249.7 | 264.3 | 279.0 | 299.6 | 317.9 | 335.7 | 351.2 | 369.8 | 390.0 | 408.1 | 415.8 | 412.5 |
| $T^{stand}$ | 208.1 | 237 | 250.4 | 267.7 | 284.7 | 299.6 | 313 | 325.7 | 338.4 | 351.5 | 368.5 | 380.7 | 386.7 |

The results obtained in accordance with the tests performed in accordance with the prior art are collated in table 4 below:

| $v_v$ | IBP | 0.05 | 0.1 | 0.2 | 0.3 | 0.4 | 0.5 | 0.6 | 0.7 | 0.8 | 0.9 | 0.95 | FBP |
|---|---|---|---|---|---|---|---|---|---|---|---|---|---|
| $T^L$ | 232.3 | 254.7 | 268.3 | 281.8 | 308.7 | 325.9 | 342.4 | 356.5 | 364.6 | 373.5 | 378.2 | 386.3 | 398.5 |
| $T^{stand}$ | 213.3 | 241.7 | 254.1 | 270.3 | 293.2 | 307.1 | 319.2 | 330.6 | 341.8 | 353.2 | 368.5 | 378.8 | 382.8 |

The covergences obtained on the one hand in accordance with the invention and on the other in accordance with the prior art were then compared.

The results obtained are collated in table 5 below:

| Samples analysed | Process | $v_v$ | | | | | |
|---|---|---|---|---|---|---|---|
| | | IBP | 10% | 20% | 50% | 90% | FBP |
| Diesel fuel | Invention | 0.7 | 0.2 | 0.5 | 0.4 | 0.7 | 1.2 |
| | Prior art | 1.66 | 1.54 | 1.0 | 1.4 | 1.7 | 1.88 |

It was thus possible to establish that the convergence obtained in accordance with the invention (0.4° C.) is twice as great as that obtained in accordance with the prior art (1° C.).

EXAMPLE 3

Construction of the TBP Distillation Curves of a Hexane-Toluene-Decane Mixture a) A hexane-toluene-decane mixture was prepared having the following volumetric composition: 45%–45%–10%.

Figure 3:
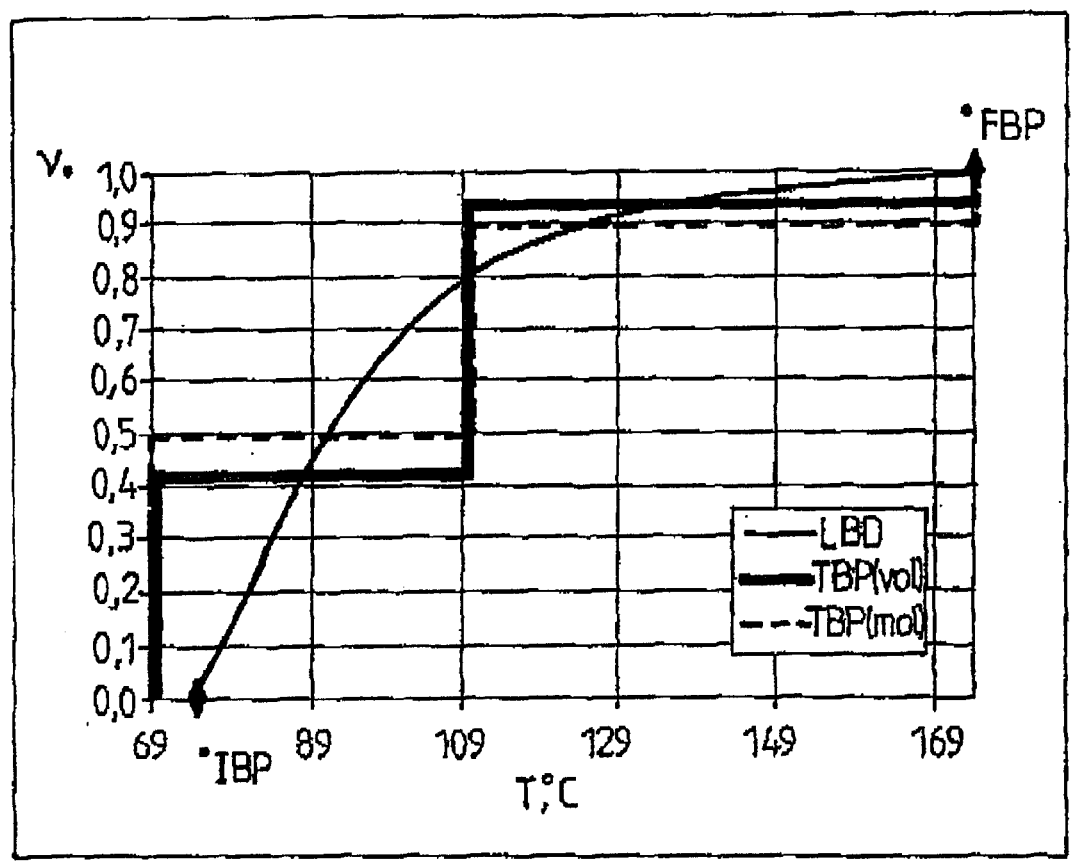

The LBD standard distillation curves and the TBP distillation curves of this mixture were plotted and are shown in FIG. 3 attached.

To establish these curves, it was considered by convention that:

$T^{HP}_{FBP}$ (LBD)=$T_{FBP}$ (TBP)

$T_{IBP}$ (TBP)=$f(S_{LBD})$

The areas situated below the curves $v_M$=f(T) (LBD) and $v_M$=f(T) (TB) are equal.

It was thus possible to define in accordance with the invention the molar relationship between the different components of the mixture.

The results obtained are collated in table 6:

| | Volumetric concentration 45-45-10 | | | | | |
|---|---|---|---|---|---|---|
| | Calculated molar fractions | | | | | Experimental molar |
| Constituents | T | a | k | $T_{IBP}$ | $T_{FBP}$ | fractions |
| Hexane | 0.405 | 9.16 | 1.4 | 75 | 174 | 0.421 |
| Toluene | 0.536 | | | | | 0.517 |
| Decane | 0.062 | | | | | 0.062 | b) A similar test was carried out from a hexane-toluene-decane mixture having the following volumetric composition: 50%–40%–10%.

Figure 4:
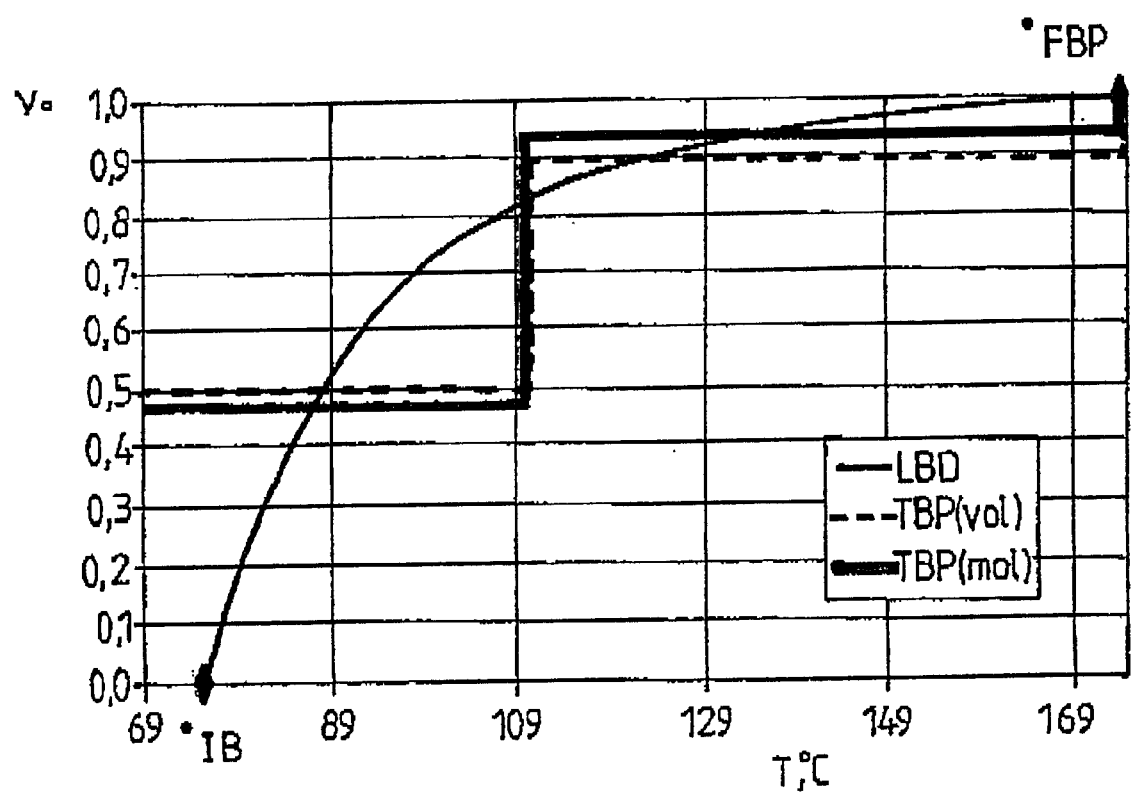

The LBD standard distillation and TBP distillation curves of this mixture were plotted; these are shown in FIG. 4 attached.

Table 7 below shows the different constituent molar fractions of this mixture which it was possible to calculate in accordance with the invention.

| | Volumetric concentration 50-40-10 | | | | | |
|---|---|---|---|---|---|---|
| | Calculated molar fractions | | | | | Experimental molar |
| Constituents | T | a | K | $T_{IBP}$ | $T_{FBP}$ | fractions |
| Hexane | 0.464 | 9.92 | 1.22 | 75 | 174 | 0.472 |
| Toluene | 0.477 | | | | | 0.464 |
| Decane | 0.059 | | | | | 0.0636 |

Tables 6 and 7 show that the invention has allowed satisfactory concordance to be obtained between the calculated volumetric fractions and the true experimental molar fractions of the initial mixture.

EXAMPLE 4

Determination of the Distillation Characteristics of a Heavy Liquid Petroleum Product Having a Boiling Temperature Higher than 400° C.

As vehicle product, a petrol was selected having the following LBP standard distillation characteristics: a=0.462; k=1.834; $T_{IBP}$=88.3° C.; and $T_{FBP}$=164.4° C.

The distillation curve v=F(T) of this vehicle liquid was established and plotted in accordance with the invention.

The results thus obtained are collated in table 8 below and shown in FIG. 5 attached.

| v | IBP | 0.072 | 0.102 | 0.137 | 0.178 | 0.223 | 0.273 | 0.327 | 0.386 | 0.451 | 0.518 | 0.591 | 0.667 | 0.747 | 0.831 | 0.9 | 0.961 | FBP |
|---|---|---|---|---|---|---|---|---|---|---|---|---|---|---|---|---|---|---|
| T | 88.3 | 107.5 | 110.9 | 114 | 117.2 | 120.1 | 122.9 | 125.7 | 128.5 | 131.3 | 134 | 136.9 | 140.1 | 143.5 | 147.5 | 151.4 | 156.3 | 164.4 |

10% of the sample of heavy petroleum product to be analysed were then added to this vehicle liquid. This mixture was also subjected to the process in accordance with the invention.

It was thus possible to determine by calculation that the LBD standard distillation parameters of this mixture were as follows: a=7.57; k=1.285; $T_{IBP}$=81° C.; and $T_{FBP}$=534.2° C.

The distillation characteristics of this mixture are collated in table 9 below and shown in FIG. 5.

| v | IBP | 0.078 | 0.11 | 0.148 | 0.191 | 0.24 | 0.294 | 0.351 | 0.414 | 0.482 | 0.554 | 0.631 | 0.711 | 0.795 | 0.874 | 0.929 | 0.973 | FBP |
|---|---|---|---|---|---|---|---|---|---|---|---|---|---|---|---|---|---|---|
| T | 81.4 | 95.5 | 100 | 106.4 | 112.5 | 119.2 | 126.7 | 135 | 144.5 | 155.5 | 168.7 | 184.6 | 205.2 | 233.8 | 273.9 | 320 | 387.7 | 534.2 |

$T^{HP}_{IBP}$ was then determined in accordance with the formula:

$$T^{HP}_{IBP} = T^1 - \Delta T^1 \cdot \left[\frac{v^i_M}{a \cdot (1 - v^i_M)}\right]^{1/k}$$

$T^{HP}_{FBP}$ was determined by iteration using the algorithm:

$$T^L_{FBP} = T^L_{END} + \frac{(T^L_{END} - T^L_{FBP})}{\left[\frac{v_{END}}{(1 - v_{END})} / a\right]^{1/k}}$$

The distillation parameters of the sample "$a^{HP}$" and "$k^{HP}$" were then defined from the additive equations:

$$\Sigma v_{MI} S_i(T^L, a_i, k_i) = S^{mix}(T^L, a^{mix}, k^{mix}) \text{ and } \Sigma v_{MI} S_i(\tau) = S^{mix}(\tau)$$

The distillation parameters of the mixture determined by calculation were as follows: "$a^{HP}$"=10.21; "$k^{HP}$"=1.54; $T^{HP}_{IBP}$=76.4° C. and $T^{HP}_{FBP}$=534.2° C.

Figure 5:
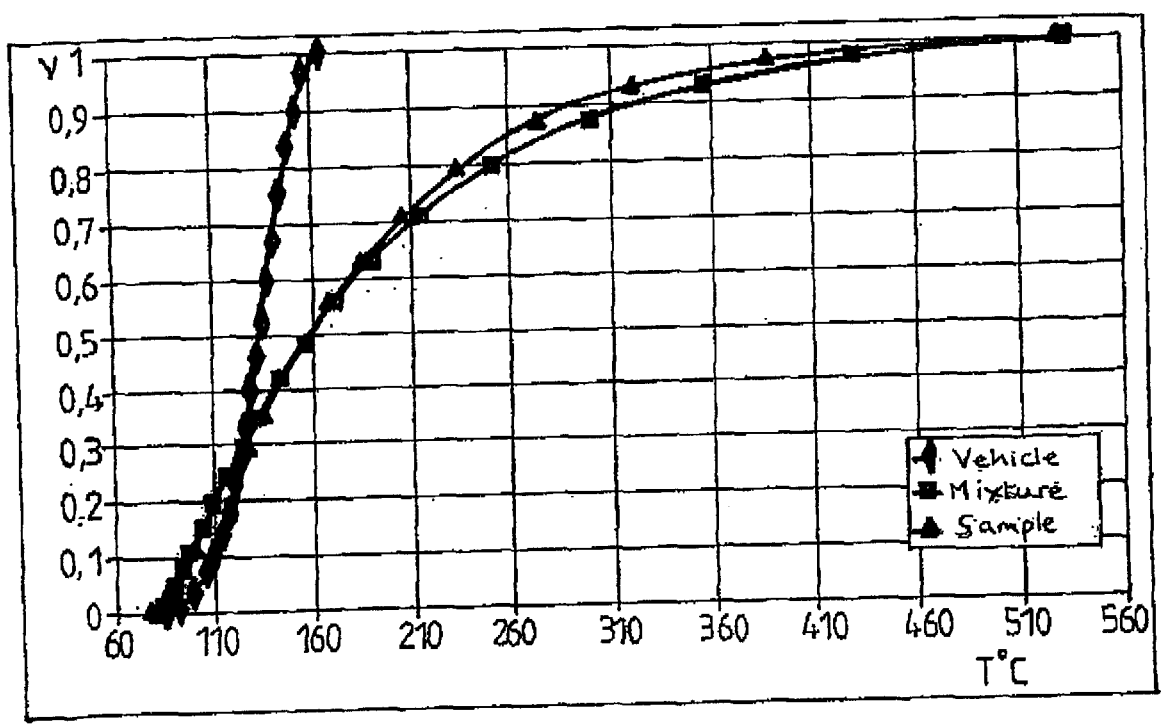

The distillation characteristics of the sample of heavy product obtained in accordance with this test are collated in table 10 below and they too are shown in FIG. 5.

| v | IBP | 0.078 | 0.11 | 0.148 | 0.19 | 0.239 | 0.292 | 0.35 | 0.412 | 0.48 | 0.55 | 0.62 | 0.707 | 0.791 | 0.87 | 0.92 | 0.97 | FBP |
|---|---|---|---|---|---|---|---|---|---|---|---|---|---|---|---|---|---|---|
| T | 77.1 | 94.33 | 98.78 | 103.8 | 109.6 | 116.2 | 123.8 | 132.6 | 142.8 | 155.2 | 170.2 | 189.7 | 214.4 | 249.9 | 299.8 | 355.2 | 429.9 | 534.2 |

What is claimed is:

1. Process for determining the distillation characteristics of liquid petroleum products by express mini distillation, characterised by the fact that it includes the following steps:

1. a volume of the order of 5 to 15 ml of the sample to be analysed is introduced into a distillation flask co-operating with a heating element at its lower part and provided with a pressure detector and two inertia-less temperature sensors permitting measurement on the one hand of the true value of the temperature of the sample in the liquid phase and on the other the true value of the temperature of the sample in the vapour phase at a level situated a little below the inlet of the outlet tube with which the distillation flask is equipped, 2. the distillation flask is heated with a constant heating intensity depending on the nature of the sample to be analysed so as to progressively boil it, 3. the vapour pressure in the distillation flask is constantly measured at the level of the inlet of the outlet tube, as are the true values of the temperatures of the sample in the liquid phase $T^L$ and the vapour phase $T^S$ and the curves are plotted representing the variations in this pressure and these temperatures as a function of time $\tau_1$, 4. the primary and secondary derivatives are established of the curve representing the variations of the temperature of the sample in the liquid phase and in the vapour phase:

$$\frac{dT^S}{d\tau_1}; \frac{dT^L}{d\tau_1}; \frac{d^2T^S}{d\tau_1^2}; \frac{d^2T^S}{d\tau_1^2}$$

and the temperature is deduced of initial boiling in the liquid phase $T^L_{IBP}$ which corresponds to the point for which $$\frac{d^2T^L}{d\tau_1^2} = 0,$$

5. the temperature of initial boiling in the vapour phase $T^S_{IBP}$ is determined which corresponds to the time for which a commencement of increase of pressure is observed.

6. the temperature $T^L_{END}$ is determined for which the value indicated by the temperature sensor which measures the true value of the temperature of the sample in the liquid phase corresponds to the value indicated by the sensor which measures the temperature of the sample in the vapour phase and by convention this temperature $T^L_{END}$ is considered to be equal to the final boiling temperature in the vapour phase $T^S_{FBP}$, 7. the volumetric percentage of sample distilled $v_V$ is determined from curves representing the variations as a function of $\tau_1$ in the pressure of vapour P in the distillation flask and in the true value of the temperature of the sample in the vapour phase $T^S$ by the function:

$$v_{Vi} = \left[\frac{Sf(Ti^S, Pi)}{Sf(T^S, P)}, V_i^{res}\right]$$

in which $Sf(T^S,P)$ depends on the area situated below the pressure curve in the distillation process while $Sf(Ti^S, Pi)$ depends on the fraction of this area at the time $\tau_{li}$, and $V_i^{res}$ represents the volume of liquid in the distillation flask at the time $\tau_{li}$, 8. the molar percentage of sample distilled $v_M$ as a function of the true value of the temperature of this sample in the vapour phase $T^S$ is determined by the function $v_{Mi}=f(v_{Vi}, \rho_i, T^S i)$ in which $\rho_i$ represents the molar density at the time $\tau_{li}$, 9. the final boiling temperature in the liquid phase $T^L_{FBP}$ is determined by interation in accordance with the formula:

$$T^L_{FBP} = T^L_{END} + \frac{(T^L_{END} - T^L_{FBP})}{\left[\frac{v_{END}}{(1 - v_{END})}\big/a\right]} 1/k$$

in which $v_{END}$ represents the molar percentage of sample distilled at the temperature $T^L_{END}$ and a and k are coefficients of the mathematical model of distillation corresponding to the empirical formula:

$$v_M = \frac{a\tau^k}{(1 + a\tau^k)}$$

calculated by iteration from the equation:

$$\ln\left(\frac{v_{Mi}}{1 - v_{Mi}}\right) = \ln a + k \ln \tau_i$$

in which:

$$\tau_i = \frac{T^L_i - T^L_{IBP}}{T^L_{FBP} - T^L_i}$$

calculating each step a new value of $T_{FBP}^L$ up to the moment when:

$$T_{FBP}^{L(n)} - T_{FBP}^{L(n-1)} \leq 1° C.$$

10. the molar percentage of sample distilled as a function of the true value of the temperature of this sample in the vapour phase is recalculated so as to take account of the residues and losses of sample in the vapour phase by the formula:

$$v_{Mi} = v'_{Mi} + \Delta Li + \Delta Si$$

in which $\Delta Si$ represents the percentage of vapour phase in the course of distillation, $\Delta Li$ the percentage of liquid phase at the moment of its formation by condensation and $v_{Mi}$ the molar percentage of sample distilled taking the residues into consideration, 11. the volumetric percentage of sample distilled $v_{Vi}$ as a function of the true value of the temperature of this sample in the liquid phase is determined by the formula:

$$v_{Vi} = f(v_{Mi}, \rho_i, T^L_i)$$

12. and the corresponding curve is traced.

2. Process as described in claim 1, characterised by the fact that the heating intensity of the heating element is adjusted so that the time required for distillation of the sample is of the order of 5 to 15 minutes.

3. Process as described in claim 1 characterised by the fact that the empirical value $T_{STAND}$ of the temperature of the sample in the vapour phase corresponding to a standard is determined from the value $T^L$ of the temperature of the sample in the liquid phase calculated at steps 1 to 12 by the formula:

$$T_{iSTAND} = T^L_i - \theta_i$$

in which $\theta$ is a function which represents the different between these temperatures.

4. Process as described in claim 3, characterised by the fact that
$T_{STAND}^{D\ 86}$ is the empirical temperature corresponding to the standard ASTM D 86 and $\theta_i^{D86}$ is calculated from the function:

$$\theta_i^{D86} = f\left(\frac{dT^L_i}{dv_{Vi}}, T^L_i, v_{vi}\right)$$

and is determined either graphically, or from values of the parameters (a, k, $T^L_{IBP}$, $T^L_{FBP}$), calculated in steps 1 to 12.

5. Process for determination by express mini distillation of the distillation characteristics of heavy liquid petroleum products having boiling temperature higher than 40020 as described in claim 1, as characterised by the fact that;
  a light vehicle liquid petroleum product is selected having a boiling temperature below 300° C. compatible with the sample to be analysed,
  this vehicle liquid is subjected to steps 1 to 12 so as to obtain the curve representing the molar percentage $v_M$ of vehicle liquid distilled as a function of the true temperature of this liquid in the liquid phase $T^L v_M$ $_{(vehicle)} = f(T^L_i)$,
  this mixture is subjected to steps 1 to 12 so as to plot the curve representing the molar percentage $v_M$ of this mixture distilled as a function of the temperature $T^L$ of this mixture in the liquid phase $v_{Mi(mix)} = f(T^L_i)$ in the same system of co-ordinates as the curve $v_{Mi(vehicle)} = f(T^L_i)$,
  it is considered by convention that the final boiling temperature $T_{FBP}^{HP}$ of the sample to be analysed is equal to the final boiling temperature of the mixture in the liquid phase, $$T_{FBP}^{HP} = T^L_{FBP}(mix)$$

$T^L_{FBP}(mix)$ is determined by interaction in accordance with steps 1 to 9, the initial boiling temperature in the liquid phase $T_{IBP}^{HP}$ of the sample to be analysed is calculated by the formula:

$$T_{IBP}^{HP} = T_1 - \Delta T_1 \left[ \frac{v_{MI}}{a^{HP}(1 - v_{MI})} \right]^{1/k^{HP}}$$

in which $T_I$ represents the temperature of intersection of the curves $v_{Mi(vehicle)} = f(T_i^L)$ and $v_{Mi(mix)} = f(T_i^L)$, $v_{Mi}$ the molar percentage of the sample which corresponds to this temperature $T_1$ and $\Delta T_1 = T_{FBP}^{HP} - T_1$ $a^{HP}$ and $k^{HP}$ are determined using the system of additive equations:

$\Sigma v_{Mi} Si(T^L, a_i, k_i) = S^{mix}(T^L, a^{mix}, k^{mix})$ and $\Sigma v_{Mi} Si(\tau) = S^{mix}(\tau)$ in which $Si(T)$ and $Si(\tau)$ are functions of the respective areas situated below the distillation curves in the systems of the co-ordinates $v_M$, T and $v_M$, $\tau$ and $\Sigma$ is a function of the specific gravity of the vehicle product in the mixture, and the curves $v_M^{HP} = f(T)$ are plotted from the formula:

$$v_M^{HP} = \frac{a^{HP} \tau^{k^{HP}}}{(1 + a^{HP} \cdot \tau^{k^{HP}})}.$$

6. Process as described in claim 5, characterised by the fact that the light vehicle liquid petroleum product consists of kerosene and/or a liquid petroleum product having a boiling point lower than 300° C.

7. Process as described in claim 1 characterised by the fact that from LBP standard distillation curves $v_M = f(T)$ corresponding to a column with a single plate, the curves of the TBP true boiling points are plotted corresponding to a technique with a column with at least 15 theoretical plates, considering by convention that the temperatures $T_{END}^L$ (LBP) and $T_{END}^L$ (TBP) are equal, that in the system of coordinates $v_M$, T the surfaces situated below the LBP standard distillation curves are equal to the areas situated below the curves of the TBP true boiling points and that $T_{LBP}$ (TBP)=$f(S_{LBP}) f(S_{LDP})$ depending on the area situated below the LBP standard distillation curve in the system of coordinates $v_M$, T.

8. Use for the implementation of the process as described in claim 1 of an apparatus characterised by the fact that it includes:

a distillation flask dimensioned to receive from 5 to 15 ml of a sample to be analysed and provided at its upper part with a bung and a lateral outlet tube cooperating with a condenser, organs for heating the distillation flask, at its lower part, with an adjustable constant heating intensity, two inertialess temperature sensors introduced into the distillation flask through pipes passing through the bung so as to permit continuous measurement, on the one hand of the true value of the temperature of a sample in the course of distillation in the liquid phase and on the other the true value of the temperature of this sample in the vapour phase at a level situated a little below the inlet of the outlet tube, a device for continuous measurement of the pressure in the vapour phase of a sample in the course of distillation which includes a pressure detector connected to the internal part of the distillation flask by a pipe passing through the bung and a capillary tube introduced into the internal part of the outlet tube at the level of the inlet of this tube, and organs for reception and exploitation of signals transmitted by the temperature sensors and the pressure detector.

9. Use as described in claim 8, characterised by the fact that:

the distillation flask is a disposable flask, and the capillary tube consists of a fixed element preferably made of stainless steel.

10. Use as described in claim 8, characterised by the fact that the apparatus forms a one-piece portable assembly.

* * * * *